United States Patent
Maruyama

(10) Patent No.: US 8,845,521 B2
(45) Date of Patent: Sep. 30, 2014

(54) TORQUE LIMITING MECHANISM OF BENDABLE PORTION CONTROL DEVICE FOR AN ENDOSCOPE

(75) Inventor: Yoshinori Maruyama, Saitama (JP)

(73) Assignee: Hoya Corporation, Tokyo (JP)

( * ) Notice: Subject to any disclaimer, the term of this patent is extended or adjusted under 35 U.S.C. 154(b) by 1389 days.

(21) Appl. No.: 11/737,291

(22) Filed: Apr. 19, 2007

(65) Prior Publication Data
US 2007/0255102 A1  Nov. 1, 2007

(30) Foreign Application Priority Data

Apr. 26, 2006 (JP) ............................ 2006-121596

(51) Int. Cl.
- *A61B 1/00* (2006.01)
- *F16D 7/04* (2006.01)
- *A61B 1/005* (2006.01)

(52) U.S. Cl.
CPC ............ *A61B 1/0052* (2013.01); *A61B 1/0057* (2013.01)
USPC ............................ 600/146; 600/148; 464/37

(58) Field of Classification Search
USPC ................. 600/106, 118, 139–142, 145–152; 403/112, 41; 464/34, 45, 37; 81/467, 81/473; 604/528; 192/41 A
See application file for complete search history.

(56) References Cited

U.S. PATENT DOCUMENTS

| | | | |
|---|---|---|---|
| 2,637,987 A * | 5/1953 | Hill et al. | 464/37 |
| 4,687,082 A * | 8/1987 | Lenfeldt | 192/55.3 |
| 5,125,143 A | 6/1992 | Takahashi | |
| 5,193,263 A | 3/1993 | Takahashi | |
| 5,388,568 A * | 2/1995 | van der Heide | 600/146 |
| 5,394,864 A | 3/1995 | Kobayashi et al. | |
| 5,496,260 A * | 3/1996 | Krauter et al. | 600/148 |
| 5,860,914 A | 1/1999 | Chiba et al. | |
| 6,439,086 B1 * | 8/2002 | Bahr | 81/467 |
| 6,439,091 B1 * | 8/2002 | Dibbern et al. | 83/543 |
| 2003/0187328 A1 * | 10/2003 | Seki et al. | 600/146 |
| 2006/0025224 A1 * | 2/2006 | Saeki et al. | 464/37 |

FOREIGN PATENT DOCUMENTS

| | | |
|---|---|---|
| JP | 55-54481 | 12/1980 |
| JP | 62-048303 | 3/1987 |
| JP | 63-238838 | 10/1988 |
| JP | 7-171093 | 7/1995 |

(Continued)

OTHER PUBLICATIONS

U.S. Appl. No. 11/737,331 to Maruyama, filed Apr. 19, 2007.

(Continued)

*Primary Examiner* — Matthew J Kasztejna
*Assistant Examiner* — Ryan Henderson
(74) *Attorney, Agent, or Firm* — Greenblum & Bernstein, P.L.C.

(57) ABSTRACT

A bendable portion control device for an endoscope including a control portion and an insertion portion extending therefrom, the insertion portion having a bendable portion at a distal end thereof, the bendable portion control device includes a control wire fixed thereto and extending to the control portion through the insertion portion; a control knob disposed on the control portion; an operating force transmission mechanism having a pair of relatively rotatable members connected to the control knob and a proximal end of the control wire, respectively; and a torque limiting mechanism for allowing torque to be transmitted to the bendable portion via the control wire when the torque is equal to or less than a predetermined torque, and for preventing the torque from being transmitted to the bendable portion via the control wire by disengaging the relatively rotatable members from each other when exceeding the predetermined torque.

6 Claims, 9 Drawing Sheets

(56) References Cited

FOREIGN PATENT DOCUMENTS

| | | | |
|---|---|---|---|
| JP | 10-295628 | 11/1998 | |
| JP | 2003-84212 | 3/2003 | |
| JP | 2003-339630 | 12/2003 | |
| WO | WO 2005010389 A1 * | 2/2005 | ............. A63H 17/26 |

OTHER PUBLICATIONS

An English language Abstract and English language computer-generated translation of JP 7-171093.

An English language Abstract and English language computer-generated translation of JP 2003-339630.

An English language Abstract and English language computer-generated translation of JP 2003-84212.

An English language Abstract and English language computer-generated translation of JP 55-54481.

U.S. Appl. No. 11/737,305 to Maruyama, filed Apr. 19, 2007.

Japan Office action, dated Jul. 13, 2011 along with an english translation thereof.

* cited by examiner

TORQUE LIMITING MECHANISM OF BENDABLE PORTION CONTROL DEVICE FOR AN ENDOSCOPE

BACKGROUND OF THE INVENTION

1. Field of the Invention

The present invention relates to a bendable portion control device (bendable portion steering device) for manipulating and steering the steerable bendable portion of a flexible insertion portion of an endoscope.

2. Description of the Related Art

In typical endoscopes, the steerable bendable portion provided in the vicinity of the distal end of the insertion portion of the endoscope can be bent freely in any direction at any angle (i.e., the orientation of the tip of the distal end can be freely adjusted) by pulling and extending control wires from a control portion coupled to the proximal end of the insertion portion of the endoscope, and the control portion is provided thereon with a freely-rotatable control knob (bendable portion control knob) for manually pulling and extending the control wires from the proximal end side thereof.

If a control wire is accidentally snapped (broken) by being acted upon by an excessive tensile force, an extremely troublesome overhaul is required; moreover, the bendable portion remains bent, which may make it difficult to remove the insertion portion of the endoscope from a body cavity safely. To prevent this problem from occurring, an endoscope in which each control wire is provided at some midpoint therein with a reduced-strength portion which is weaker in strength than the control wire has been proposed. In this endoscope, the reduced-strength portion breaks upon an excessive tensile force acts on the control wire. This structure is disclosed in, e.g., Japanese unexamined patent publication 2003-339630.

On the other hand, in conventional endoscopes in which the control wires are pulled and extended by a motor(s), an endoscope which is provided between the motor and the proximal end of an associated control wire with a friction clutch which slips upon a load over a predetermined load being exerted so that the bendable portion may not push a parietal (somatic wall) excessively hard and so that an excessive load is not exerted on the motor is known in the art. This type of endoscope is disclosed in, e.g., Japanese examined utility-model publication S55-54481.

However, as disclosed in JUPP 2003-339630, even if the aforementioned reduced-strength portion that is weaker in strength than the control wire is installed at some midpoint therein, the reduced-strength portion breaks upon the bendable portion control knob being rotated with an excessive torque. Once the reduced-strength portion breaks, the broken part needs to be fixed, so that the endoscopic operation cannot continue to be performed at any rate.

As disclosed in JEUMP S55-54481, in the configuration in which the aforementioned friction clutch that slips upon a load over a predetermined load being exerted is provided, a cork disk serving as a frictional member needs to be sandwiched between two metal disks, and additionally, a disk spring (belleville spring) or the like for setting an appropriate frictional force needs to be provided to be overlaid on the metal disks having the cork disk therebetween. Due to this structure, even if the friction clutch can be installed in a portion of the endoscope which does not have to be directly manually operated like a motor drive mechanism, the bendable portion control knob increases in size to thereby deteriorate the operability of the endoscope if one intends to install the friction clutch into, e.g., the internal space of the bendable portion control knob that is manually operated to manipulate the bendable portion. This increase in size of the bendable portion control knob results in a serious loss in the operability of the endoscope.

SUMMARY OF THE INVENTION

The present invention provides a bendable portion control device of an endoscope which makes it possible for the endoscope to continue to be used without being damaged even if an excessive torque is exerted on the bendable portion control knob during use of the endoscope, and further makes it possible to achieve this bendable portion control device by a mechanism which is sufficiently small and thin so as to be capable of being installed in, e.g., the internal space of the bendable portion control knob.

According to an aspect of the present invention, a bendable portion control device is provided, for an endoscope including a control portion and an insertion portion extending from the control portion, the insertion portion having a bendable portion at a distal end thereof, the bendable portion control device including a control wire, a distal end of which is fixed to the bendable portion and which is extended to the control portion through the insertion portion; a manually-rotatable control knob disposed on the control portion for pulling the control wire to bend the bendable portion; an operating force transmission mechanism for transmitting a torque exerted on the control knob to the bendable portion via the control wire, the operating force transmission mechanism having a pair of relatively rotatable members one and the other of which are connected to the control knob and a proximal end of the control wire, respectively; and a torque limiting mechanism for allowing the torque to be transmitted to the bendable portion via the control wire by holding the pair of relatively rotatable members engaged with each other when the torque is one of equal to and less than a predetermined torque, and for preventing the torque from being transmitted to the bendable portion via the control wire by disengaging the pair of relatively rotatable members from each other when the torque exceeds the predetermined torque.

It is desirable for the torque limiting mechanism to be accommodated and arranged in an internal space of the control knob. Hence, the torque limiting mechanism can be easily made slim.

It is desirable for one and the other of the pair of relatively rotatable members to include a grooved rotational plate rotatable about an axis thereof, at least one engaging groove being formed in one of an outer peripheral surface and an inner peripheral surface of the grooved rotational plate; and at least one spring engaging arm made of a resilient material which is positioned along the one of the outer peripheral surface and the inner peripheral surface of the grooved rotational plate, in which the engaging groove is formed, to be freely rotatable relative to the grooved rotational plate. At least one engaging lug is provided on the spring engaging arm so as to project therefrom to be capable of being engaged in and disengaged from the engaging groove.

It is desirable for the engaging lug to project from the spring engaging arm at a free end thereof, and for the spring engaging arm to be resiliently deformed to make the engaging lug disengaged from the engaging groove upon the torque exceeding the predetermined torque.

It is desirable for the grooved rotational plate to be provided on a member to which the control wire is connected, for the engaging groove to be formed on an outer peripheral surface of the grooved rotational plate, and for the spring engaging arm to be provided on another member connected to the control knob.

It is desirable for the grooved rotational plate to be provided on a member connected to the control knob, for the engaging groove to be formed on an inner peripheral surface of the grooved rotational plate, and for the spring engaging arm to be provided on another member to which the control wire is connected.

It is desirable for the bendable portion control device to include a second spring engaging arm which is positioned along the one of the outer peripheral surface and the inner peripheral surface of the grooved rotational plate to be resiliently pressed against the one of the outer peripheral surface and the inner peripheral surface of the grooved rotational plate.

In a state where the engaging lug is disengaged from the engaging groove, it is desirable for the spring engaging arm to be in sliding contact with the grooved rotational plate to produce a frictional resistance between the spring engaging arm and the grooved rotational plate due to resiliency of the spring engaging arm when a relative rotation occurs between the grooved rotational plate and the spring engaging arm.

It is desirable for the spring engaging arm and the grooved rotational plate to not be in contact with each other in a state where the engaging lug is disengaged from the engaging groove.

It is desirable for the torque limiting mechanism to lie in a plane orthogonal to an axis of rotation of the control knob.

It is desirable for the operating force transmission mechanism to includes a cylindrical shaft fixed to a stationary member of the control portion to extend upright coaxially with an axis of the control knob; a tubular drive shaft positioned around the cylindrical shaft to be freely rotatable on an axis of the cylindrical shaft; and a pulley fixed to the tubular drive shaft, the proximal end of the control wire being fixed to the pulley. The grooved rotational plate is fixed to the tubular drive shaft.

It is desirable for the spring engaging arm and the second spring engaging arm to be integral to be formed as a substantially C-shaped ring.

According to the present invention, since the bendable portion control device is provided with a torque limiting mechanism, positioned in the operating force transmission mechanism, for allowing a torque which is exerted on the control knob to be transmitted to the bendable portion via the control wire when the torque is at or below a predetermined torque and for preventing the torque from being transmitted to the bendable portion via the control wire when the torque is over the predetermined torque, the endoscope can continue to be used without being damaged even if an excessive torque is exerted on the bendable portion control knob during use of the endoscope; moreover, this bendable portion control device can be achieved by the small and thin torque limiting mechanism which is sufficiently small and thin so as to be capable of being installed in, e.g., the internal space of the bendable portion control knob that is manually operated to manipulate the bendable portion.

The present disclosure relates to subject matter contained in Japanese Patent Application No. 2006-121596 (filed on Apr. 26, 2006) which is expressly incorporated herein in its entirety.

BRIEF DESCRIPTION OF THE DRAWINGS

The present invention will be described below in detail with reference to the accompanying drawings in which.

DESCRIPTION OF THE PREFERRED EMBODIMENTS

Figure 3:
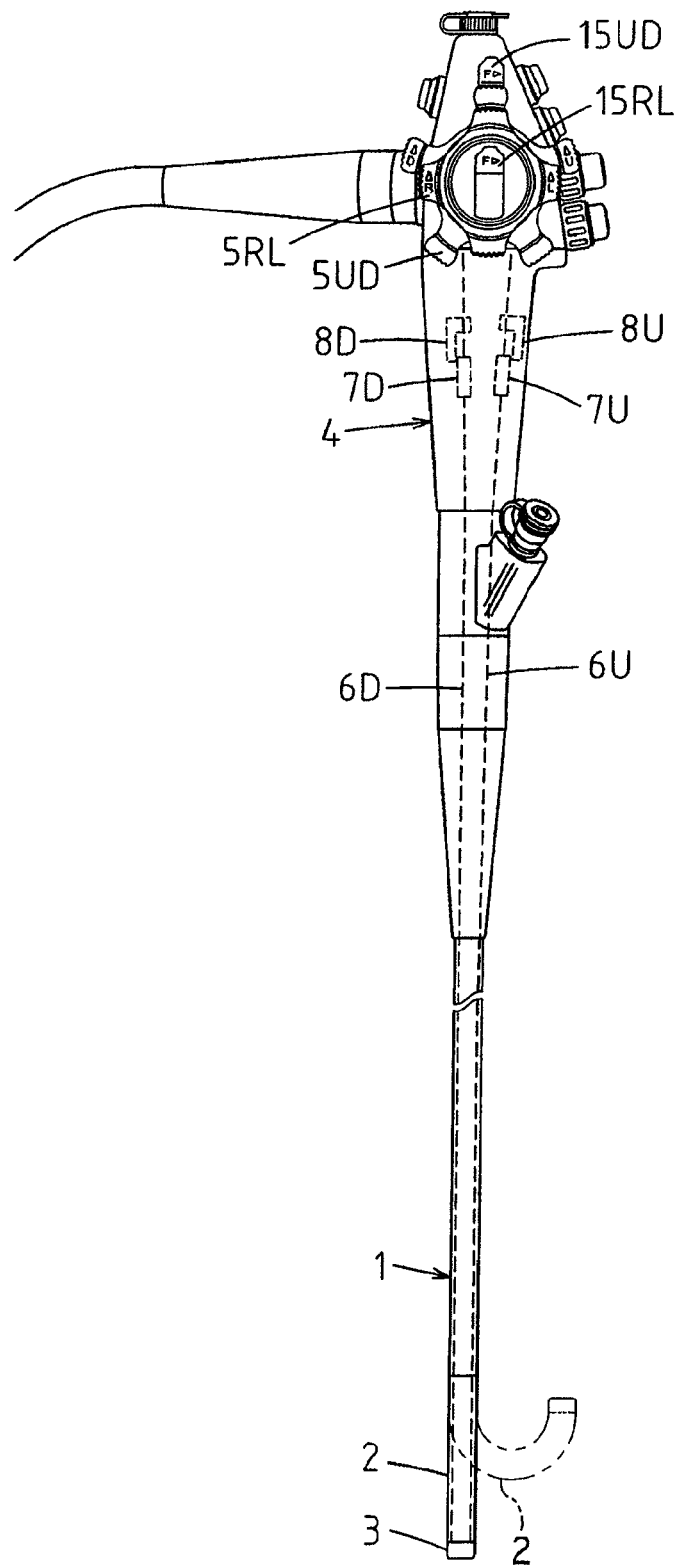
FIG. 3 shows the outward appearance of the first embodiment of the endoscope, showing the overall structure thereof.

FIG. 3 shows the general configuration of a first embodiment of the endoscope. The endoscope is provided with a flexible insertion portion 1 and a control portion 4 coupled to the proximal end of the insertion portion 1. The insertion portion 1 is provided in the vicinity of the distal end (free end) thereof with a remote-controllable bendable portion 2, and is further provided with an end body 3 fixed to the end (free end) of the bendable portion 2. An objective window and others (not shown) are provided in the end body 3.

The control portion 4, which is coupled to the proximal end of the insertion portion 1, is provided thereon with a U-D control knob 5UD for bending the bendable portion 2 upward and downward in a controlled manner, and an R-L control knob 5RL for bending the bendable portion 2 rightward and leftward in a controlled manner. The U-D control knob 5UD and the R-L control knob 5RL are overlaid on each other and coaxially arranged so that each of the U-D control knob 5UD and the R-L control knob 5RL can be freely rotated on a common axis.

An upward-direction control wire 6U and a downward-direction control wire 6D are inserted into the insertion portion 1 and distal ends thereof and are fixed to the end body 3. Turning the U-D control knob 5UD counterclockwise causes the upward-direction control wire 6U to be pulled toward the control portion 4 to thereby cause the bendable portion 2 to bend upward (e.g., upward direction of a monitoring screen which corresponds to forward direction of the control portion 4) as shown by two-dot chain lines in FIG. 3. Turning the U-D control knob 5UD clockwise causes the downward-direction control wire 6D to be pulled toward the control portion 4 to thereby cause the bendable portion 2 to bend downward.

Additionally, turning the R-L control knob 5RL counterclockwise causes a leftward-direction control wire 6L (FIG. 4), which is inserted into the insertion portion 1 to be installed therein, to be pulled toward the control portion 4 to thereby cause the bendable portion 2 to bend leftward. Turning the R-L control knob 5RL clockwise causes a rightward-direction control wire 6R (FIG. 4), which is installed in the insertion portion 1, to be pulled toward the control portion 4 to thereby cause the bendable portion 2 to bend rightward. In this manner, the bendable portion 2 can be remote-controlled to be bent freely in any directions at any angle from the control portion 4 side.

The endoscope is provided, at midpositions of the upward-direction control wire 6U and the downward-direction control wire 6D inside of the control portion 4, with two slack removing devices 7U and 7D which move with the upward-direction control wire 6U and the downward-direction control wire 6D to absorb slack thereof which occur when the upward-direction control wire 6U and the downward-direction control wire 6D are extended toward the bendable portion 2 from the U-D control knob 5UD (in a direction opposite to the direction in which the upward-direction control wire 6U and the downward-direction control wire 6D are pulled), respectively, and the endoscope is further provided inside of the control portion 4 with two stationary stoppers 8U and 8D against which the two slack removing devices 7U and 7D abut when the upward-direction control wire 6U and the downward-direction control wire 6D are pulled to respective predetermined positions to prevent the upward-direction control wire 6U and the downward-direction control wire 6D from being pulled therebeyond, respectively. The control portion 4 is provided with a U-D brake control knob 15UD and an R-L brake control knob 15RL which are coaxially arranged with the U-D control knob 5UD and the R-L control knob 5RL. The U-D brake control knob 15UD is operated to actuate a U-D brake mechanism 14 (see FIG. 4) to lock the upward control wire 6D and the downward-direction control wire 6D, and the R-L brake control knob 15RL is operated to actuate an R-L brake mechanism (not shown) to lock the leftward-direction control wire 6L and the rightward-direction control wire 6R.

Figure 4:
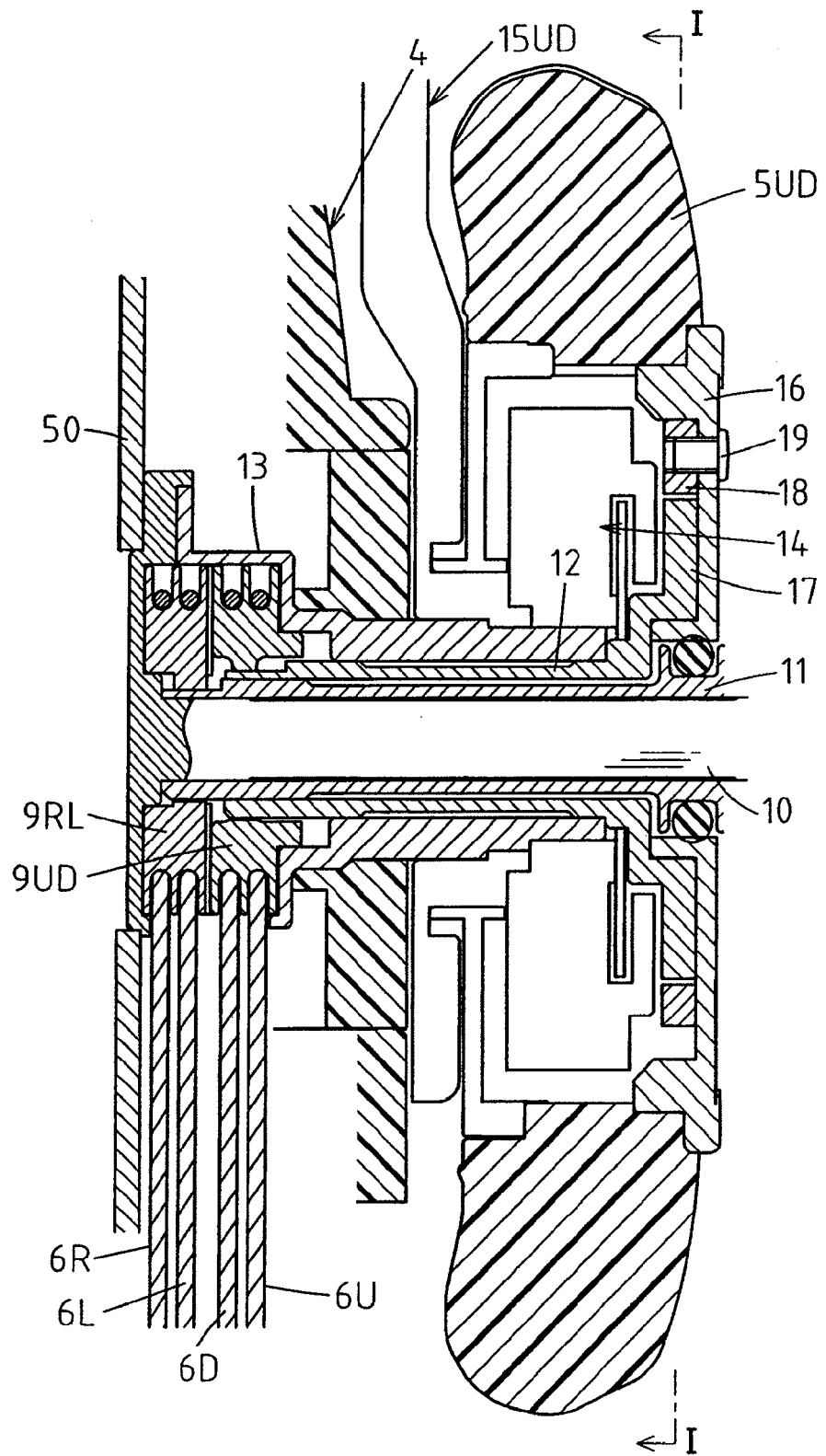
FIG. 4 is a longitudinal cross sectional view of an operating force transmission mechanism of the bendable portion control device of the first embodiment of the endoscope.

FIG. 4 shows an operating force transmission mechanism of a bendable portion control device (bendable portion steering device) provided between the U-D control knob 5UD and the proximal ends of the upward-direction control wire 6U and the downward-direction control wire 6D. The U-D control knob 5UD is formed so that a ring-shaped control portion thereof has a large internal space, and a supporting column (cylindrical shaft) 10 of the operating force transmission mechanism is fixed to an internal main frame 50 of the control portion 4 to extend upright coaxially with the axis of the U-D control knob 5UD.

As shown in FIG. 4, the operating force transmission mechanism is provided with a U-D pulley 9UD having two outer peripheral grooves in which the upward-direction control wire 6U and the downward-direction control wire 6D are engaged and wound around the U-D pulley 9UD by a half to one turn and extend therefrom toward the bendable portion 2. The operating force transmission mechanism is also provided with an R-L pulley 9RL, similar in structure to the U-D pulley 9UD, having two outer peripheral grooves in which the leftward-direction control wire 6L and the rightward-direction control wire 6R are engaged to be wound around the R-L pulley 9RL by a half to one turn and extend therefrom toward the bendable portion 2.

An R-L tubular drive shaft 11 fixed at one end thereof to the R-L pulley 9RL is rotatably fitted on the supporting column 10 and a U-D tubular drive shaft 12 fixed at one end thereof to the U-D pulley 9UD is rotatably fitted on the R-L tubular drive shaft 11. In order to transmit rotations of the R-L control knob 5RL and the U-D control knob 5UD to the R-L pulley 9RL and the U-D pulley 9UD, the R-L tubular drive shaft 11 and the U-D tubular drive shaft 12 project outwards (upwards as viewed in FIG. 4) from the control portion 4 so that the other ends thereof are positioned outside of the control portion 4 to be associated with the R-L control knob 5RL and the U-D control knob 5UD, respectively.

A cylindrical U-D bearing 13 in which the U-D tubular drive shaft 12 is fitted to be freely rotatable on the axis thereof is fixed at the base end of the U-D bearing 13 to a base of the supporting column 10 which is fixed to the internal main frame 50 of the control portion 4. The U-D bearing 13 also serves as a pulley cover which covers the R-L pulley 9RL and the U-D pulley 9UD to prevent the control wires 6U and 6D and the control wires 6R and 6L from being disengaged from the U-D pulley 9UD and the R-L pulley 9RL, respectively.

Rotating the U-D tubular drive shaft 12 about the axis thereof (on the axis of the supporting column 10) causes the U-D pulley 9UD to rotate to thereby pull one of the control wires 6U and 6D in accordance the direction of rotation of the U-D tubular drive shaft 12.

The U-D brake mechanism 14 gives frictional resistance to the rotating operation of the U-D control knob 5UD about the axis thereof so that the bendable portion 2 remains stationary in a bent state. The U-D brake mechanism 14 is installed and accommodated in an internal space of the U-D control knob 5UD and operated to give frictional resistance to the rotating operation of the U-D control knob 5UD and release the same frictional resistance selectively via operation of the U-D brake control knob 15UD.

A substantially disk-shaped seating plate 16 that is integral with the U-D control knob 5UD is positioned thereon to close an outer open end of the internal space of the U-D control knob 5UD, and an outer end surface of a grooved rotational plate (relatively rotatable member) 17 made of metal which is formed integral with the U-D tubular drive shaft 12 is in sliding contact with an inner surface of the seating plate 16 to be freely rotatable on the axis of the grooved rotational plate 17.

Figure 1:
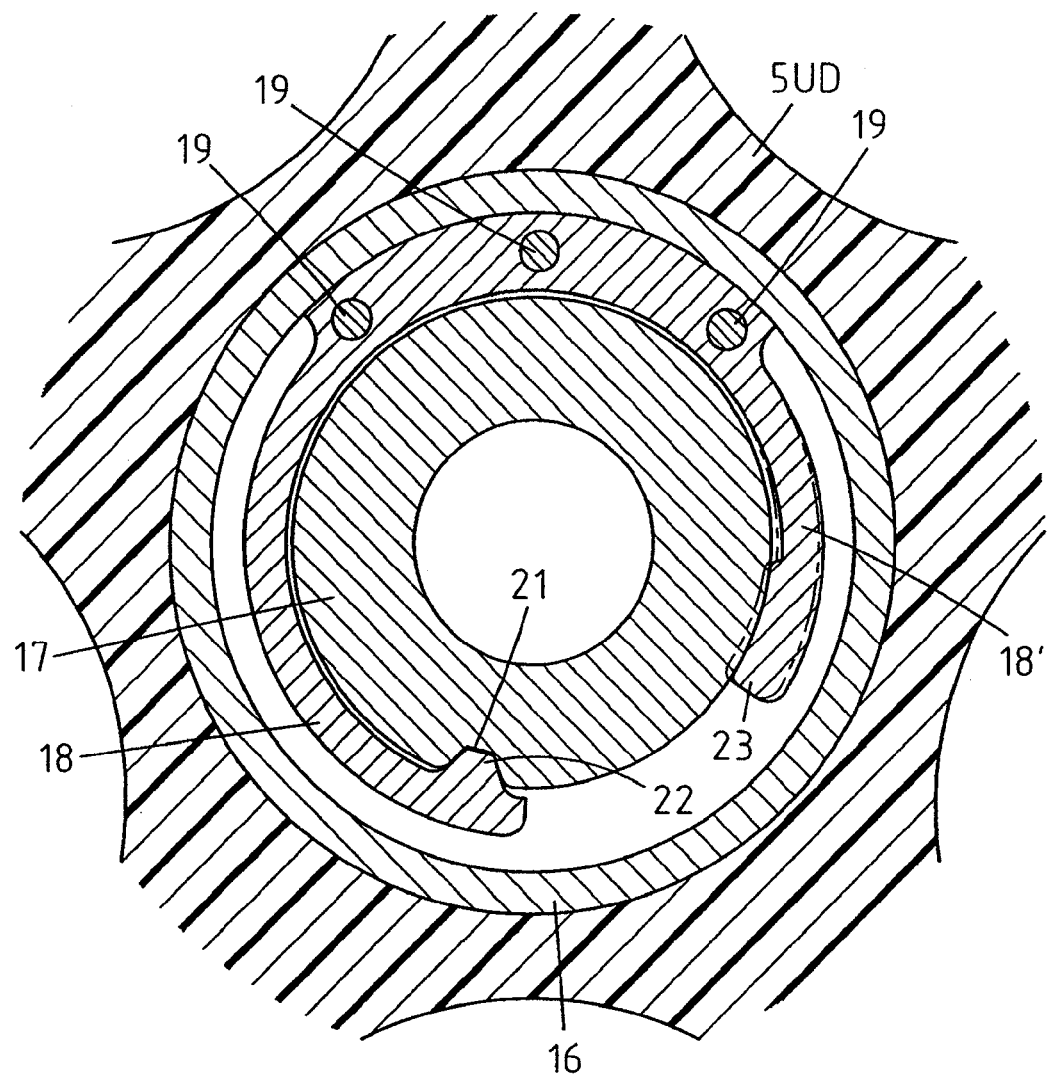
FIG. 1 is a cross sectional view of a torque limiting mechanism provided in a bendable portion control device of a first embodiment of an endoscope according to the present invention (taken along I-I line in FIG. 4)

As also shown in FIG. 1, that shows a cross sectional view taken along I-I line in FIG. 4, the grooved rotational plate 17, the outer edge of which is formed in a circular shape as a whole, is provided on a part of an outer peripheral surface thereof with an engaging groove (notch) 21. An arc-shaped spring engaging arm (relatively rotatable member) 18 made of a resilient material is fixed at a base end portion thereof to the seating plate 16 by three set crews 19 to be positioned around an outer periphery of the grooved rotational plate 17. The spring engaging arm 18 is provided at a free end thereof with an engaging lug 22 which projects radially inwards to be freely capable of being engaged in and disengaged from the engaging groove 21 of the grooved rotational plate 17.

When no external force is applied to the spring engaging arm 18, the spring engaging arm 18 is set in a state shown in FIG. 1 where the engaging lug 22 is engaged in the engaging groove 21 of the grooved rotational plate 17. The spring engaging arm 18 in this state can freely rotate integrally with the seating plate 16 about the axis of the thereof, and the engaging lug 22 remains engaged in the engaging groove 21 of the grooved rotational plate 17 when a torque exerted on the U-D control knob 5UD is equal to or less than a predetermined torque.

Accordingly, when the U-D control knob 5UD is manually rotated, the spring engaging arm 18 rotates with the seating plate 16 to thereby cause the grooved rotational plate 17 to rotate, so that the rotational control force exerted on the U-D control knob 5UD is transmitted to the control wires 6U and 6D via the U-D tubular drive shaft 12 and others.

Figure 2:
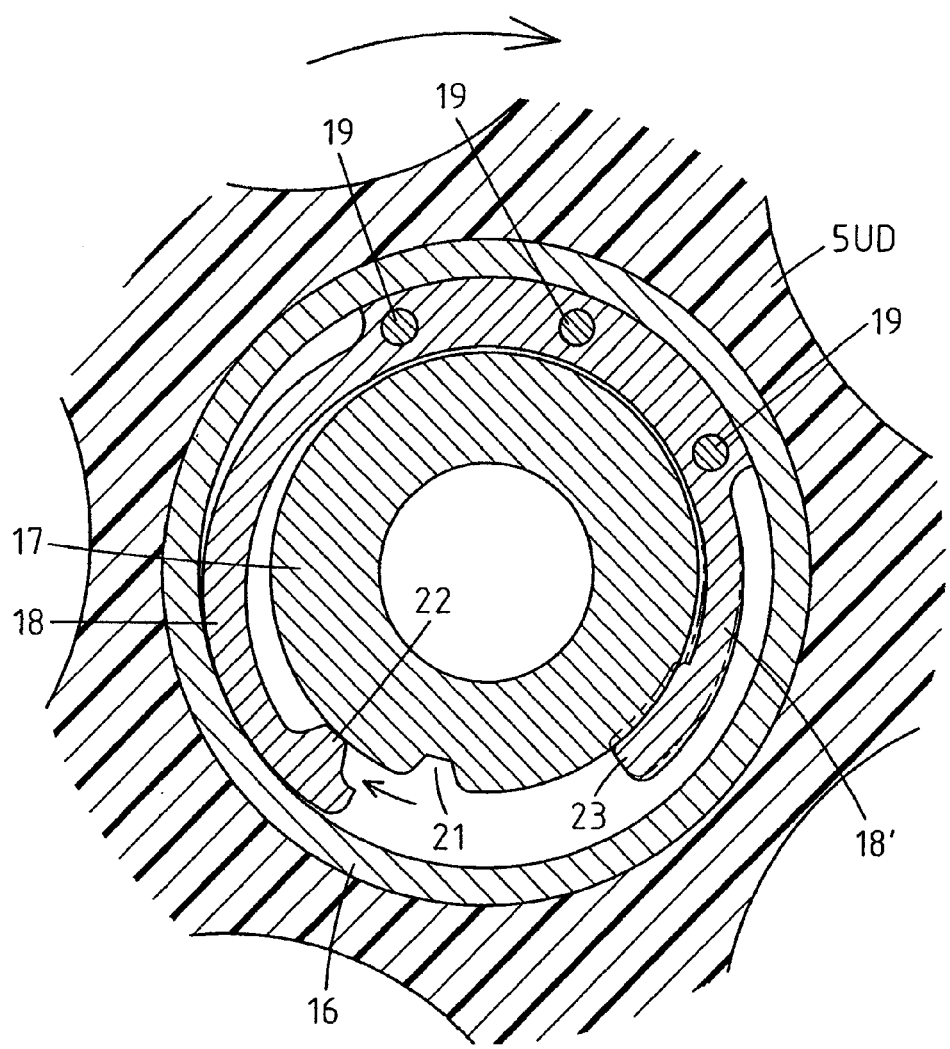
FIG. 2 is a cross sectional view of the torque limiting mechanism shown in FIG. 1 in an operational state.

Upon an excessive control force exceeding the aforementioned predetermined torque being exerted on the U-D control knob 5UD, the spring engaging arm 18 is resiliently deformed to make the engaging lug 22 disengaged from the engaging groove 21 of the grooved rotational plate 17 as shown in FIG. 2, so that the grooved rotational plate 17 does not rotate with the seating plate 16 even if the seating plate 16 rotates, and consequently, a rotational force exerted on the U-D control knob 5UD is not transmitted to the control wires 6U and 6D. Accordingly, even if an excessive torque is exerted on the U-D control knob 5UD, the endoscope (control wires 6U and 6D) is not damaged.

If the engagement of the engaging groove 21 of the grooved rotational plate 17 with the engaging lug 22 is released in the above-described manner, the bendable portion control device shown in FIGS. 1 and 2 can be brought back to a state where the engaging lug 22 is engaged in the engaging groove 21 of the grooved rotational plate 17 if the U-D control knob 5UD is manually rotated after the grooved rotational plate 17 has been locked so that it cannot freely rotate about the axis thereof by actuating the aforementioned brake mechanism 14, which makes it possible to allow the endoscopic operation to continue to be performed normally.

In this manner, the grooved rotational plate 17 (in which the engaging groove 21 is made) and the spring engaging arm 18 (on which the engaging lug 22 is formed) constitute a torque limiting mechanism for allowing a torque exerted on the U-D control knob 5UD to be transmitted to the bendable portion 2 via the control wires 6U and 6D when the torque is equal to or less than a predetermined torque and for preventing a torque exerted on the U-D control knob 5UD from being transmitted to the bendable portion 2 via the control wires 6U and 6D when the torque exceeds the predetermined torque. As shown in FIG. 4, this torque limiting mechanism is sufficiently thin and small so as to be capable of being installed in a small space in the U-D control knob 5UD. The torque limiting mechanism lies in a plane orthogonal to the common axis of rotation of the U-D control knob 5UD and the R-L control knob 5RL.

In this particular embodiment of the endoscope, a second spring engaging arm 18' extends from the base end portion of the spring engaging arm 18 to be positioned around an outer periphery of the grooved rotational plate 17, similar to the spring engaging arm 18. The spring engaging arm 18 and the second spring engaging arm 18' are formed integral with each other so as to form a substantially C-shaped ring. The second spring engaging arm 18' is provided at a free end thereof with a pressure projection 23 which projects radially inwards to be resiliently brought into pressing and sliding contact with an outer peripheral surface of the grooved rotational plate 17. The second spring engaging arm 18' is formed to be shorter in length than the spring engaging arm 18 that is provided with the engaging lug 22.

Due to this structure, frictional resistance occurs between the grooved rotational plate 17 and an outer peripheral surface of the pressure projection 23 not only in a state as shown in FIG. 1 where the engaging lug 22 is engaged in the engaging groove 21 of the grooved rotational plate 17 but also in a state as shown in FIG. 2 where the engaging lug 22 is disengaged from the engaging groove 21. Due to this frictional resistance, as long as either of the control wires 6U and 6D is not acted upon by a repulsive force from the bendable portion 2 or the like, manually rotating the U-D control knob 5UD causes the grooved rotational plate 17 to rotate to some extent, thus causing the upward-direction control wire 6U or the downward-direction control wire 6D to be pulled so that the bendable portion 2 is bent to a certain extent.

Figure 5:
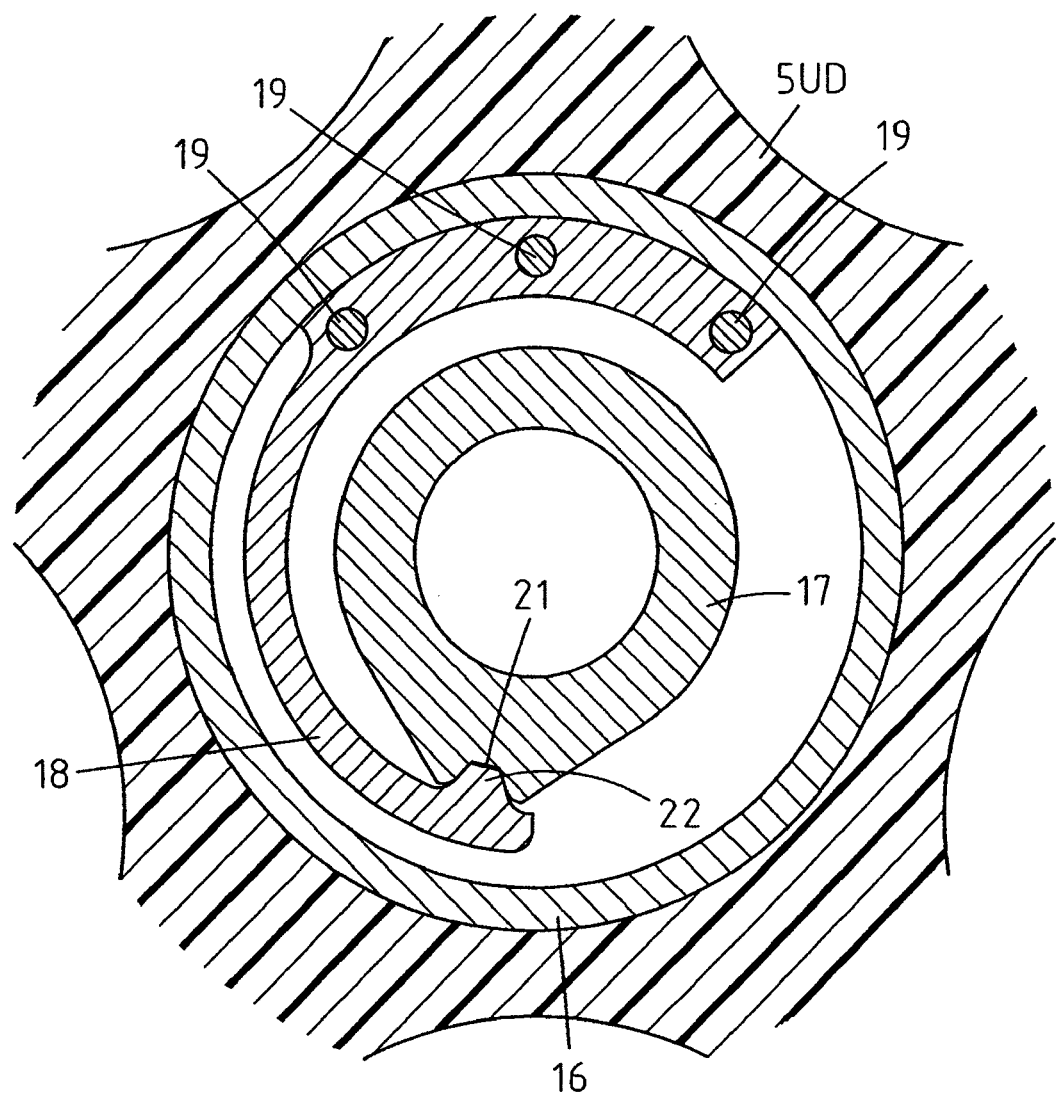
FIG. 5 is a cross sectional view of a torque limiting mechanism provided in the bendable portion control device of a second embodiment of the endoscope according to the present invention (taken along a section corresponding to the section shown by I-I line in FIG. 4)

FIG. 5 shows a cross sectional view of the torque limiting mechanism provided in the bendable portion control device of a second embodiment of the endoscope according to the present invention, taken along a section corresponding to the section shown by I-I line in FIG. 4. The torque limiting mechanism shown in FIG. 5 is constructed so that the outer diameter of the grooved rotational plate 17 is reduced to a degree that the outer peripheral surface of the grooved rotational plate 17 does not come in contact with the engaging lug 22 to allow the U-D control knob 5UD to rotate freely with no resistance upon the engaging lug 22 being disengaged from the engaging groove 21. This structure facilitates the operation of bringing the engaging lug 22 back into the engaging groove 21.

Figure 6:
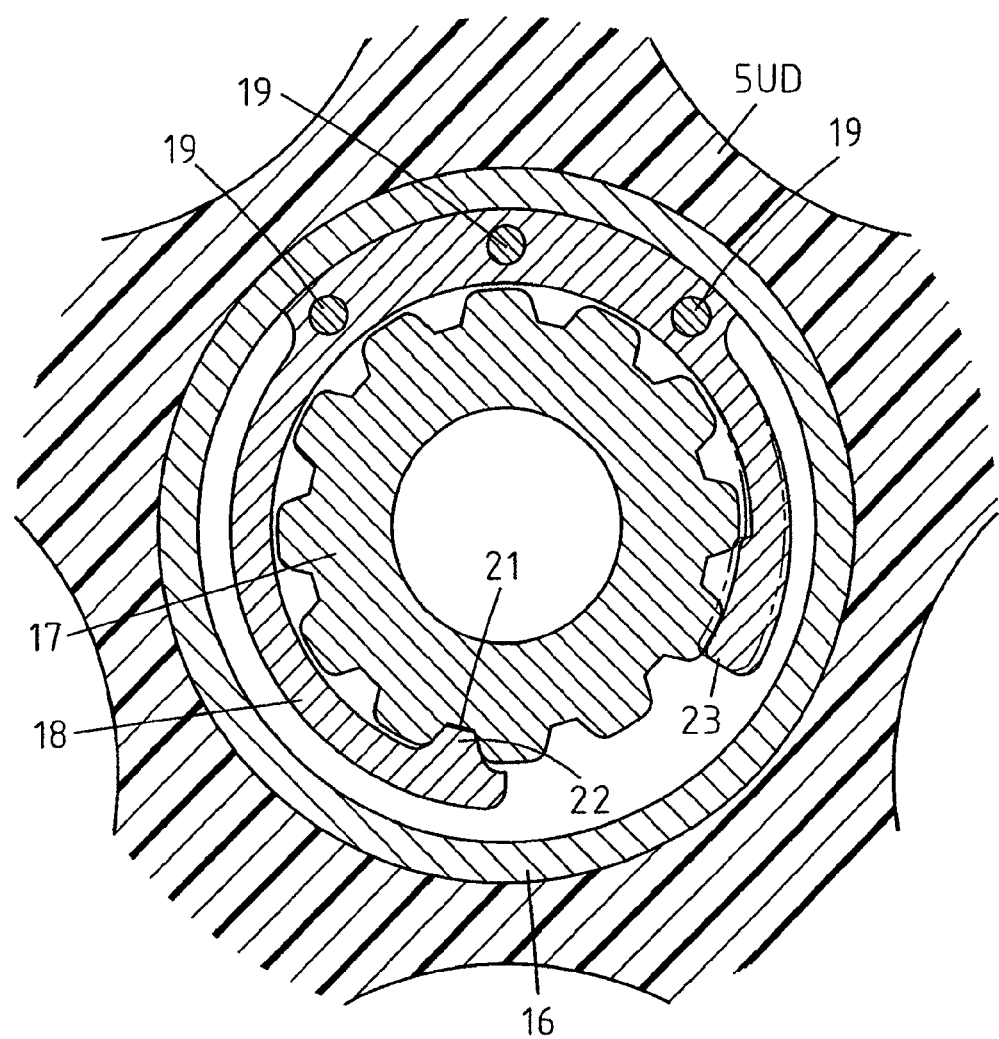
FIG. 6 is a cross sectional view of a torque limiting mechanism provided in the bendable portion control device of a third embodiment of the endoscope according to the present invention (taken along a section corresponding to the section shown by I-I line in FIG. 4)

FIG. 6 shows the torque limiting mechanism provided in the bendable portion control device of a third embodiment of the endoscope according to the present invention. In this embodiment, the grooved rotational plate 17 is provided with a plurality of engaging grooves 21, each into which the engaging lug 22 is engageable. According to this structure, even when the engaging lug 22 is disengaged from one engaging groove 21, the engaging lug 22 is immediately re-engaged in another engaging groove 21 so that the bendable portion 2 returns to a controllable state thereof without delay.

Figure 7:
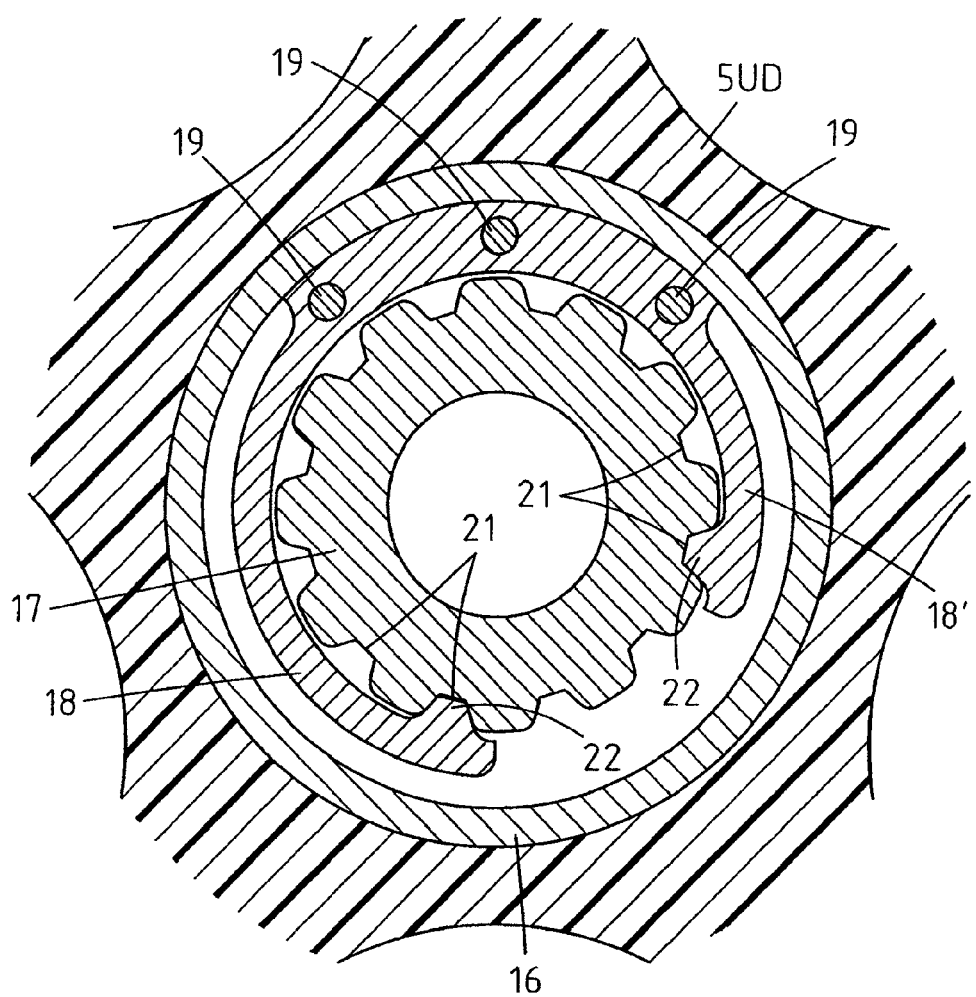
FIG. 7 is a cross sectional view of a torque limiting mechanism provided in the bendable portion control device of a fourth embodiment of the endoscope according to the present invention (taken along a section corresponding to the section shown by I-I line in FIG. 4)

FIG. 7 shows the torque limiting mechanism provided in the bendable portion control device of a fourth embodiment of the endoscope according to the present invention. In this embodiment, not only the grooved rotational plate 17 is provided with a plurality of engaging grooves 21 in each of which the engaging lug 22 is engageable just like the grooved rotational plate 17 shown in FIG. 6 but also the second spring engaging arm 18' is provided at a free end thereof with an engaging lug 22 which projects radially inwards to be freely capable of engaging in and disengaged from each engaging groove 21 of the grooved rotational plate 17. With this structure, the engaging force between the engaging lug 22 and the engaging groove 21 in which the engaging lug 22 is engaged (i.e., the limit value of the torque at which the engaging lug 22 is disengaged from the engaging groove 21) can be set at a large force.

Figure 8:
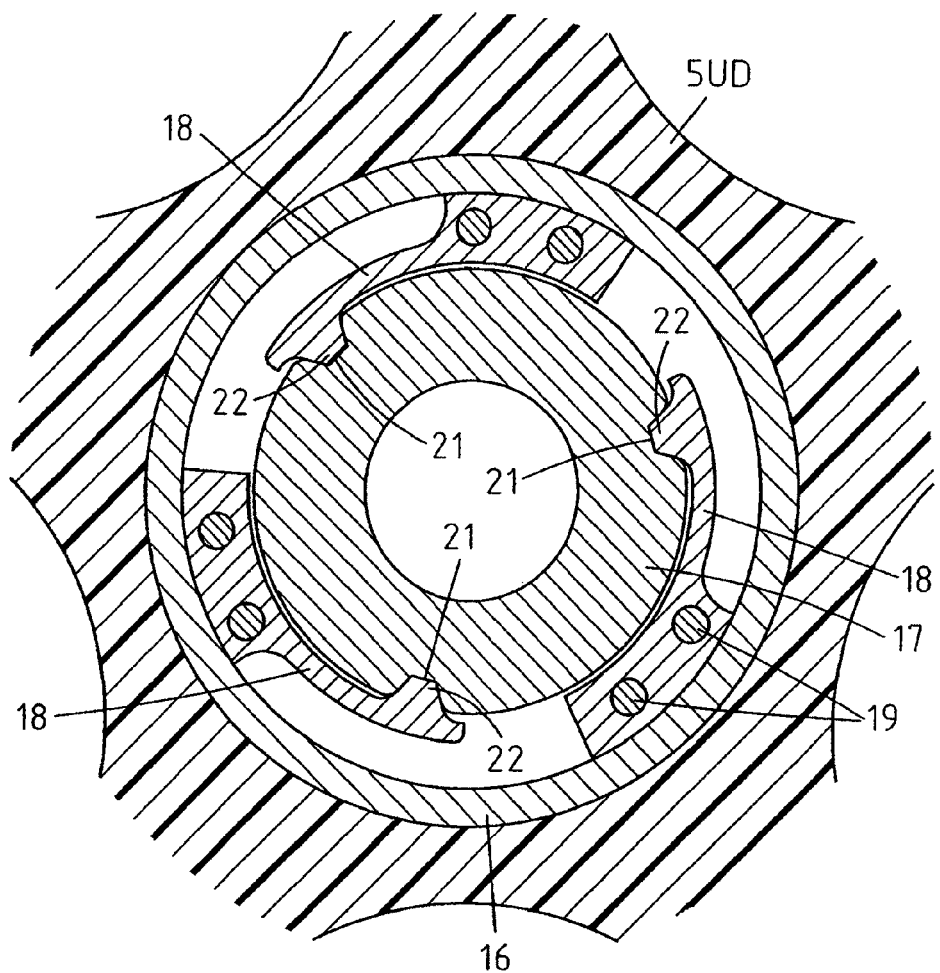
FIG. 8 is a cross sectional view of a torque limiting mechanism provided in the bendable portion control device of a fifth embodiment of the endoscope according to the present invention (taken along a section corresponding to the section shown by I-I line in FIG. 4)

FIG. 8 shows the torque limiting mechanism provided in the bendable portion control device of a fifth embodiment of the endoscope according to the present invention. In this embodiment, the grooved rotational plate 17 is provided, on the outer peripheral surface thereof at substantially equiangular intervals with a plurality of engaging grooves (notches) 21 (specifically three grooves in this particular embodiment), while a corresponding plurality of spring engaging arms 18 (specifically three spring engaging arms in this particular embodiment), each of which is provided at the free end thereof with an engaging lug 22 which projects radially inwards to be freely capable of being engaged in and disengaged from each engaging groove 21 are provided around the grooved rotational plate 17. The torque limiting mechanism can be constructed in this manner to achieve a great engaging force between the engaging lugs 22 and the engaging grooves 21.

Figure 9:
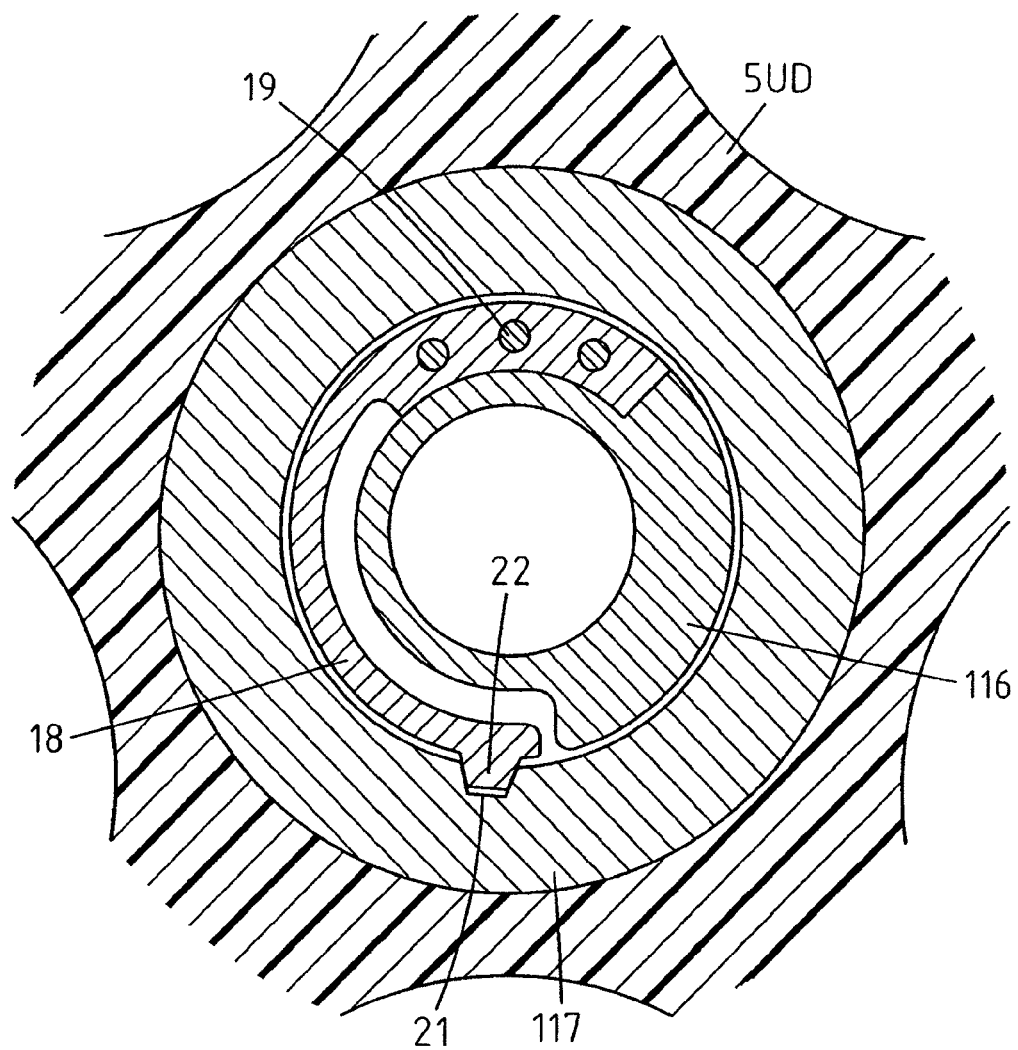
FIG. 9 is a cross sectional view of a torque limiting mechanism provided in the bendable portion control device of a sixth embodiment of the endoscope according to the present invention (taken along a section corresponding to the section shown by I-I line in FIG. 4).

FIG. 9 shows the torque limiting mechanism provided in the bendable portion control device of a sixth embodiment of the endoscope according to the present invention. In this embodiment, a grooved rotational plate 117 which is provided on an inner peripheral surface thereof with an engaging groove (notch) 21 is configured to rotate with the U-D control knob 5UD, and a seating plate 116 which is provided on an outer peripheral surface thereof with an engaging lug 22 which projects radially outwards to be freely engageable in the engaging groove 21 is formed integral with the U-D tubular drive shaft 12 to which the upward-direction control wire 6U and the downward-direction control wire 6D are connected via the U-D direction pulley 9UD. It is possible that the relative position between the engaging groove 21 and the engaging lug 22 be reversed in this manner in each of the above described embodiments.

The present invention is not limited solely to each of the above described particular embodiments. For instance, the torque limiting mechanism provided in each of the above described particular embodiments can also be applied to the other bendable portion control device (bendable portion steering device) provided between the R-L control knob 5RL and the proximal ends of the rightward-direction control wire 6R and the leftward-direction control wire 6L.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A bendable portion control device for an endoscope including a control portion and an insertion portion extending from the control portion, the insertion portion having a distal end bendable portion provided at a distal end of the insertion portion, the bendable portion control device comprising:
    a control wire, a distal end of which is fixed to the distal end bendable portion, and the control wire extending to the control portion through the insertion portion;
    a manually-rotatable control knob provided on the control portion, the manually-rotatable control knob configured to pull the control wire so as to bend the distal bendable portion;
    an operating force transmission mechanism that transmits a torque exerted on the control knob to the distal end bendable portion via the control wire, the operating force transmission mechanism having a grooved rotational plate and a seating plate, the grooved rotational plate and the seating plate being relatively rotatable with respect to each other, the seating plate being connected to one of the control knob and a proximal end of the control wire, and the grooved rotational plate being connected to the other of the control knob and the proximal end of the control wire,
    the grooved rotational plate having at least one engaging groove formed in one of the outer and inner peripheral surfaces of the grooved rotational plate,
    at least one spring engaging arm having an end fixed to the seating plate and positioned along the one of the outer and inner peripheral surfaces of the grooved rotational plate in which the at least one engaging groove is formed, the at least one spring engaging arm comprising a resilient material, wherein the at least one spring engaging arm is rotatable relative to the grooved rotational plate,
    at least one engaging lug provided on and projecting from a free end of the at least one spring engaging arm so as to engage and disengage the at least one engaging groove;
    a torque limiting mechanism defined by the interaction between the grooved rotational plate and the at least one spring engaging arm,
    wherein the at least one engaging lug is positioned within the at least one engaging groove when an applied torque is one of equal to and less than a predetermined torque,
    wherein the at least one spring engaging arm resiliently deforms such that the at least one engaging lug disengages the at least one engaging groove when the applied torque exceeds the predetermined torque, and
    wherein the at least one spring engaging arm comprises first and second spring engaging arms which are positioned along the one of the outer and inner peripheral surfaces of the grooved rotational plate so as to be resiliently pressed against the one of the outer and the inner peripheral surfaces of the grooved rotational plate,
    the first and second spring engaging arms are integrally formed so as to provide a substantially C-shaped ring,
    the at least one lug is provided on the first spring engaging arm; and
    a pressure projection provided on the second spring engaging arm, wherein the pressure projection slidably contacts the grooved rotational plate so as not to be positioned within a corresponding groove when that at least one spring engaging arm is engaged with the at least one engaging groove.

2. The bendable portion control device according to claim 1, wherein the torque limiting mechanism is provided within an internal space of the control knob.

3. The bendable portion control device according to claim 1, wherein the grooved rotational plate is provided on a member to which the control wire is connected,
    wherein the at least one engaging groove is formed on an outer peripheral surface of the grooved rotational plate, and
    wherein the at least one spring engaging arm is provided on another member connected to the control knob.

4. The bendable portion control device according to claim 1, wherein, in a state where the at least one engaging lug is disengaged from the at least one engaging groove, the at least one spring engaging arm is in sliding contact with the grooved rotational plate to produce a frictional resistance between the at least one spring engaging arm and the grooved rotational plate due to resiliency of the at least one spring engaging arm when a relative rotation occurs between the grooved rotational plate and the at least one spring engaging arm.

5. The bendable portion control device according to claim 1, wherein the torque limiting mechanism lies in a plane orthogonal to an axis of rotation of the control knob.

6. The bendable portion control device according to claim 1, wherein the operating force transmission mechanism comprises:
    a cylindrical shaft fixed to a stationary member of the control portion to extend upright coaxially with an axis of the control knob;
    a tubular drive shaft positioned around the cylindrical shaft to be rotatable on an axis of the cylindrical shaft; and
    a pulley fixed to the tubular drive shaft, the proximal end of the control wire being fixed to the pulley,
    wherein the grooved rotational plate is fixed to the tubular drive shaft.

* * * * *